United States Patent [19]

Saito et al.

[11] 4,367,286

[45] Jan. 4, 1983

[54] REFERENCE BLOOD FILTER PAPER FOR MEASURING THE CONCENTRATION OF METHIONINE IN THE BLOOD

[75] Inventors: Yoshitada Saito, Oomiya; Akira Yano, Tokorozawa; Yasushi Kasahara, Tama, all of Japan

[73] Assignee: Fujizoki Pharmaceutical Co., Ltd., Tokyo, Japan

[21] Appl. No.: 300,753

[22] Filed: Sep. 10, 1981

[30] Foreign Application Priority Data

Sep. 19, 1980 [JP] Japan ................................ 55-129149

[51] Int. Cl.³ ........................ G01N 33/68; C12Q 1/00
[52] U.S. Cl. ........................................ 435/29; 422/56; 435/188; 435/805; 435/839
[58] Field of Search ...................... 435/18, 23, 29, 32, 435/33, 188, 260, 805, 839; 422/56

[56] References Cited

U.S. PATENT DOCUMENTS 3,245,882  4/1966  Guthrie ............................ 422/56 X

FOREIGN PATENT DOCUMENTS 53-15485  2/1978  Japan ................................. 435/260

*Primary Examiner*—Arnold Turk
*Attorney, Agent, or Firm*—Burgess, Ryan and Wayne

[57] ABSTRACT

A reference blood filter paper for measuring the concentration of methionine in the blood, comprising a piece of blood filter paper, a blood material infiltered in the blood filter paper containing a known concentration of methionine and at least one water-soluble, sulfur-containing antioxidant represented by general formula:

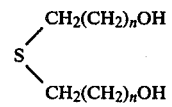

where $n = 1$ or 2.

3 Claims, No Drawings

REFERENCE BLOOD FILTER PAPER FOR MEASURING THE CONCENTRATION OF METHIONINE IN THE BLOOD

BACKGROUND OF THE INVENTION

The present invention relates to a reference blood filter paper for diagnosis of homocystinuria, one kind of congenital disorder of amino acid metabolism, and more particularly to a reference blood filter paper of the kind mentioned above, which is used for the diagnosis of homocystinuria by measuring the concentration of methionine in the blood, and which can be preserved for a long period of time without any detectable deterioration.

Congenital disorders of amino acid metabolism, such as phenylketonuria, histidinemia and homocystinuria, are fearful diseases leading to mental deficiency or hepatocirrhosis. These days, however, patients with such congenital disorders can be cured and their lives saved if the disorders are identified during early infancy and the patients are promptly and appropriately treated, for instance, by subjecting them to dietary treatment.

In order to identify those disorders, it is necessary that the concentration of a particular amino acid in the blood of a new born baby be measured within a week after its birth, to determine whether or not that concentration is abnormally high. For this purpose, there is desired a simple and reliable screening assay.

The assay which is in most general use for this determination of concentration at preset is Guthrie's Bacterial Inhibition Assay. The principle of that assay is as follows:

When bacillus subtilis is cultured in an agar culture medium, if the agar culture medium contains a predetermined amount of a metabolism inhibitor which works on an amino acid which is indispensable to the growth of bacillus subtilis, the growth of bacillus subtilis will be inhibited by the action of the metabolism inhibitor. However, when a piece of filter paper into which sample blood has been infiltrated is placed on the above-mentioned agar culture medium containing the metabolism inhibitor, and bacillus subtilis is cultured there, bacillus subtilis can grow, utilizing the amino acid contained in the blood in the filter paper, so that a growth circle of bacillus subtilis, corresponding in size to the quantity of the amino acid contained in the blood, is formed.

Likewise, bacillus subtilis is cultured on a piece of reference blood filter paper into which blood containing a known amount of the amino acid has been infiltrated, so that a reference growth circle of bacillus subtilis is obtained.

By comparing the first mentioned growth circle with the second mentioned reference growth circle, the approximate concentration of the amino acid in the sample blood can be determined.

The details of this procedure and measurement conditions for the Guthrie's Bacterial Inhibition Assay are described in Rinshobyori (Clinical Pathology) 24 (12) 962–973, 1976.

In order to obtain highly stable and reproducible measurement results, it is indispensable that the amount of the amino acid contained in the reference blood filter paper not change with time, and the reference blood filter paper be preservable for a long period of time without any detectable deterioration.

In a conventional reference blood filter for measuring the concentration of methionine in the blood, methionine contained in the reference blood filter is oxidized extremely easily during preservation and, accordingly, its properties also change during preservation.

For instance, when it is preserved at a temperature of $-20°$ C., it is so deteriorated after 4 months that it cannot be used any longer. This is a significant shortcoming of the conventional reference blood filter paper.

SUMMARY OF THE INVENTION

It is therefore an object of the present invention to provide a novel reference blood filter paper for measuring the concentration of methionine in the blood, which reference blood filter paper is free from the shortcomings of the conventional blood filter paper and can be preserved for a long period of time without any detectable deterioration.

The present invention is based on the discovery that an organic, water-soluble, sulfur-containing antioxidant with a sulfide structure, such as $\beta$-thiodiglycol and $\beta$-thiodipropanol, is capable of preventing methionine contained in the dried blood from being oxidized or changed in properties, without having any adverse effects on the growth of bacillus subtilis which serves as an indicator of the quantity of methionine contained in the blood.

In the present invention, one of the above-mentioned antioxidants is used in the reference blood filter paper in order to attain the above-mentioned object of the present invention.

DETAILED DESCRIPTION OF THE PREFERRED EMBODIMENTS

As the organic, water-soluble, sulfur-containing antioxidant having a sulfide structure that can be employed in the present invention, $\beta$-thiodiglycol and $\beta$-thiodipropanol can be employed.

An embodiment of a piece of reference blood filter paper according to the present invention is prepared as follows:

The above-mentioned antioxidant is dissolved in the waste blood of healthy persons so as to yield a mixture of the blood and the antioxidant, containing 30 mM to 120 mM of the antioxidant, preferably 35 mM to 60 mM of the antioxidant, therein.

L-methionine is dissolved in the above-mentioned mixture to yield a mixture with a total concentration of 1 mg/dl of L-methionine. Likewise, six other mixtures with the total concentrations of L-methionine being 2 mg/dl, 4 mg/dl, 8 mg/dl, 12 mg/dl, 16 mg/dl and 20 mg/dl are prepared.

Each mixture is softly stirred and is then allowed to stand for 2 hours at room temperature so as to disperse the antioxidant and L-methionine homogeneously in the mixture.

Each mixture is spread on a commercially available filter paper for diagnosis of phenylketonuria (PKU) with a diameter of 11 mm and is then air-dried, whereby a piece of reference blood filter paper according to the present invention is prepared. For use as a reference blood filter paper for Guthrie's Bacterial Inhibition Assay when the concentration of L-methionine in the blood of a patient is to be measured, a piece of the blood filter paper with a diameter of 3 mm is cut from the above-mentioned blood filter paper by use of a disc puncher.

Unlike the conventional reference blood filter paper, the reference blood filter paper according to the present invention can be preserved without any detectable deterioration for more than one year at −20° C. or more than 6 months at 4° C., and, when preserved under the above-mentioned conditions, can provide a growth circle in accordance with each specified concentration of L-methionine, without having any adverse effects on the necessary factors for Guthrie's Bacterial Inhibition Assay, such as the growth of bacillus subtilis and the color of the blood.

In Table 1, there are shown the results of comparisons between the blood filter paper according to the present invention and blood filter papers in which antioxidants other than the antioxidants according to the present invention are employed, in terms of the effects of the antioxidants on the blood when each blood filter paper is prepared and on the growth of bacillus subtilis in the Guthrie's Bacterial Inhibition Assay.

TABLE 1

| Antioxidant | Effects on the Blood | Effects on Guthrie's BIA* | Suitability |
|---|---|---|---|
| β-thiodiglycol | In concentrations up to 120 mM, no coagulation of the blood and no change in color of the blood. | In concentrations up to 120 mM, no formation of an inhibition circle and no difference in growth of bacillus subtilis between the addition of this antioxidant and no addition thereof. | Suitable |
| β-thiodipropanol | In concentrations up to 120 mM, no coagulation of the blood and no change in color of the blood. | In concentrations up to 120 mM, no formation of an inhibition circle and no difference in growth of bacillus subtilis between the addition of this antioxidant and no addition thereof. | Suitable |
| Thioglycolic Acid | Above 15 mM, immediate coagulation of the blood, the color thereof changing to dark brown. | Excessive growth of bacillus subtilis not corresponding to the growth of amino acid. | Unsuitable |
| β, β'-thiodipropionic acid | Above 10 mM, immediate coagulation of the blood, the color thereof changing to dark brown. | — | Unsuitable |
| Dithiothreitol | Above 45 mM, coagulation of the blood in 2 hrs., the color thereof changing to dark brown. | Above 15 mM, conspicuous formation of an inhibition circle. | Unsuitable |
| 2-mercaptoethyl alcohol | Above 45 mM, coagulation of the blood in 2 hrs., the color thereof changing to dark brown. | Above 15 mM, conspicuous formation of an inhibition circle. | Unsuitable |

| Antioxidant | Effects on the Blood | Effects on Gurhrie's Assay | Suitability |
|---|---|---|---|
| Sodium thiosulfate | The color of the blood changes to that of fresh blood. | Above 30 mM, formation of an inhibition circle is recognized. | Unsuitable |
| Sodium hydrosulfite | Above 10 mM, the color of the blood changes to dark purple. | — | Unsuitable |
| Buthylated hydroxyanisole | Practically insoluble in water and difficult to handle. | Forms the same growth circle regardless of the concentration of methionine. | Unsuitable |
| Buthylated hydroxytoluene | Practically insoluble in water and difficult to handle. | Forms the same growth circle regardless of the concentration of methionine. | Unsuitable |
| EDTA.2Na | | Above 0.1 mM, inhibition of the growth of bacillus subtilis is conspicuous. | Unsuitable |

Note:
*Bacterial Inhibition Assay

TABLE 2

| Added Amount of Methionine | Antioxidant Kind | Antioxidant Added Amount | Duration of Stability Test at 37° C. (days) | | | | |
|---|---|---|---|---|---|---|---|
| | | | 2 | 7 | 14 | 22 | 37 |
| L-methionine 4 mg/dl | No addition for comparison | 0 | 3.6 mg/dl (90%) | 2.84 (71) | 2.64 (66) | 2.56 (64) | 2.44 (61) |
| | β-thiodiglycol | 50 mM | 3.96 mg/dl (99%) | 3.76 (94) | 3.60 (90) | 3.44 (86) | 3.32 (83) |
| | β-thiodipropanol | 50 mM | 3.97 mg/dl (99%) | 3.80 (97) | 3.62 (91) | 3.40 (85) | 3.29 (82) |
| L-methionine 12 mg/dl | No addition for comparison | 0 | 10.8 mg/dl (90%) | 9.6 (80) | 9.48 (79) | 9.36 (78) | 8.78 (73) |
| | β-thiodiglycol | 50 mM | 11.76 mg/dl (98%) | 11.52 (96) | 11.16 (93) | 10.92 (91) | 10.80 (90) |
| | β-thiodipro- | 50 mM | 11.81 mg/dl | 11.59 | 11.20 | 10.88 | 10.82 |

TABLE 2-continued

| Added Amount of Methionine | Antioxidant Kind | Antioxidant Added Amount | Duration of Stability Test at 37° C. (days) | | | | |
|---|---|---|---|---|---|---|---|
| | | | 2 | 7 | 14 | 22 | 37 |
| | panol | | (98%) | (97) | (93) | (91) | (90) |

Note:
Figures in the table indicate the found concentration of residual methionine.
Figures in parentheses indicate the ratio of the residual methionine to the amount of methionine added.

Referring to Table 1, the antioxidants which cause coagulation of the blood are not suitable for the object of the present invention since, if the coagulation takes place, the blood is not absorbed homogenously in the blood filter paper. Furthermore, the antioxidants which change the color of the blood placed on the reference blood filter paper to the extent that the color is quite different from the color of the blood to be tested, or the antioxidants which form inhibition circles inhibiting the growth of bacillus subtilis, are not suitable for the present invention since they may cause erroneous judgements in the comparative observations of the growth of bacillus subtilis in the Guthrie's Bacterial Inhibition Assay.

As a matter of course, the antioxidants which inhibit the growth of bacillus subtilis or which promote the growth of the same in such a manner as to be irrelevant to the concentration of methionine contained in the blood, cannot be used in practice, either.

The comparative results shown in Table 1 show that the antioxidants suitable for the present invention are $\beta$-thiodiglycol and $\beta$-thiodipropanol.

Referring to Table 2, there are shown the results of tests conducted as to the stability of L-methionine in the reference blood filter papers containing the above-mentioned antioxidants according to the present invention, which were conducted under severe conditions at 37° C. In Table 2, the quantitative measurement of the remaining L-methionine was conducted by Bioassay employing lactobacillus.

It is empirically known that reference blood filter paper which can hold therein more than 80% of L-methionine after severe testing for 14 days can be preserved for more than one year at −20° C. and can then be used without any problems for the Guthrie's Bacterial Inhibition Assay. From this empirical knowledge, the results in Table 2 show that the reference blood filter paper produced by use of the blood to which 50 mM of $\beta$-thiodiglycol or $\beta$-thiodipropanol is added can be safely preserved for more than one year at −20° C.

Referring to Table 3, there are shown the results of tests for investigation of the relationship between the amount of each of $\beta$-thiodiglycol and $\beta$-thiodipropanol and the preservation effect thereof, which were conducted under the same conditions as the tests summarized in Table 2.

TABLE 3

| Filter Paper | Duration of Preseruation at 37° C. | Concentration of Antioxidant | | | | |
|---|---|---|---|---|---|---|
| | | 15 mM | 30 | 60 | 90 | 120 |
| (1) Addition of $\beta$-thiodiglycol | | | | | | |
| With methionine in concentration of 4 mg/dl | 14 days | 3.16 mg/dl (79%) | 3.60 (90) | 3.60 (90) | 3.64 (91) | 3.60 (90) |
| | 28 days | 3.12 (78) | 3.36 (84) | 3.40 (85) | 3.44 (86) | 3.44 (86) |
| With methionine in concentration of 12 mg/dl | 14 days | 10.20 mg/dl (85%) | 11.28 (94) | 11.28 (94) | 11.40 (95) | 11.40 (95) |
| | 28 days | 9.84 (82) | 10.80 (90) | 10.80 (90) | 10.92 (91) | 10.92 (91) |
| (2) Addition of $\beta$-thiodipropanol | | | | | | |
| With methionine in concentration of 4 mg/dl | 14 days | 3.12 mg/dl (78%) | 3.44 (86) | 3.68 (92) | 3.72 (93) | 3.68 (92) |
| | 28 days | 3.00 (75) | 3.28 (82) | 3.48 (87) | 3.52 (88) | 3.52 (88) |
| With methionine in concentration of 12 mg/dl | 14 days | 9.96 mg/dl (83%) | 10.80 (90) | 11.28 (94) | 11.28 (94) | 11.52 (96) |
| | 28 days | 9.72 (81) | 10.44 (87) | 10.92 (91) | 10.82 (90) | 11.16 (93) |

As can be seen from Table 3, when more than 30 mM of one of the antioxidants is added, the residual ratio of L-methionine in the blood filter paper is more than 80% and, therefore, by the addition of that amount of one of the antioxidants, the preservation effect for the object of the present invention can be sufficiently attained.

The present invention will now be explained more specifically by referring to the following examples of embodiments thereof.

EXAMPLE 1

6 l of the waste blood (with Hematocrit Value being 42%) of healthy persons was centrifuged at 2000 rpm for 20 minutes. From the centrifuged blood, 402 ml of the supernatant solution, blood plasma, was removed by suction, in order to adjust the Hematocrit Value of the remaining blood solution to be 55%.

25 ml of $\beta$-thiodiglycol with a purity of 98% was placed in a 5-l volumetric flask. To the $\beta$-thiodiglycol was added the above-mentioned blood solution to yield exactly 5 l of a mixture of the blood and $\beta$-thiodiglycol. In the blood mixture, the concentration of $\beta$-thiodiglycol was 49 mM/l.

The concentration of L-methionine in the blood mixture was measured by an automatic amino acid detector to be 0.25 mg/dl.

Seven L-methionine solutions with different concentrations of L-methionine were prepared and one ml of each solution was placed in each of seven 100-ml volumetric flasks. Into each flask was placed the above-mentioned blood solution containing the antioxidant in such a manner as to yield exactly mixtures of 100 ml with the total concentrations of L-methionine being 1 mg/dl, 2 mg/dl, 4 mg/dl, 8 mg/dl, 12 mg/dl, 16 mg/dl and 20 mg/dl.

Each of the mixtures was softly stirred and was then allowed to stand for 2 hours at room temperature in order to disperse the L-methionine homogenously throughout the mixture.

50 μl of each of the mixture was dropped on pieces of the filter paper for PKU diagnosis manufactured by Toyo Filter Paper Co., Ltd., in such a manner that the dropped mixture spread in a circle with a diameter of 11 mm.

Each filter paper was dried at room temperature for about 2 hours and was then dried in a vacuum dryer and finally laminated.

The thus prepared filter papers were preserved for 6 months and one year at −20° C. and were compared with the conventional filter papers in terms of the growth circle of bacillus subtilis in the Guthrie's Bacterial Inhibition Assay.

The results are shown in the following table:

| Concentration of Methionine | | Antioxidant | Immediately after production | Preservation for 6 months | Preservation for one year |
| --- | --- | --- | --- | --- | --- |
| 4 mg/dl | Conventional product | 0 | 25.2 mm | 23.7 (+) | 20.5 (+) |
| | Product of the present invention | β-thiodiglycol 49 mM | 25.5 mm | 25.0 | 25.0 |
| 12 mg/dl | Conventional product | 0 | 35.0 mm | 32.5 | 30.0 (+) |
| | Product of the present invention | β-thiodiglycol 49 mM | 35.0 mm | 34.8 | 35.0 |

(Note)
(+) indicates the formation of an inhibition circle.

EXAMPLE 2

7.0 ml of β-thiodipropanol was placed in a 1-l volumetric flask and the blood solution with the Hematocrit Value of 55%, prepared in Example 1, was added to the β-thiodipropanol to yield exactly 1 l of the mixture. The concentration of the antioxidant, β-thiodipropanol, was 50 mM in the mixture. Exactly in the same manner as in Example 1, a predetermined different amount of L-methionine was added to each blood solution to form blood mixtures with different concentrations of L-methionine and each mixture was dropped on each piece of the previously mentioned filter paper for PKU diagnosis.

Each filter paper was dried to prepare a reference blood filter paper.

The thus prepared filter papers were preserved for 6 months and one year at −20° C. and were compared with the conventional filter papers in terms of the growth circle of bacillus subtilis in the Guthrie's Bacterial Inhibition Assay.

The results are shown in the following table.

| Concentration of Methionine | | Antioxidant | Immediately after production | Preservation for 6 months | Preservation for one year |
| --- | --- | --- | --- | --- | --- |
| 4 mg/dl | Conventional product | 0 | 25.0 mm | 23.7 mm | 21.0 mm |
| | Product of the present invention | β-thiodipropanol 50 mM | 25.0 | 24.8 | 25.0 |
| 12 mg/dl | Conventional product | 0 | 35.0 | 32.5 | 30.0 |
| | Product of the present invention | β-thiodipropanol 50 mM | 35.0 | 35.2 | 34.8 |

(Note)
Figures in the above table indicate the diameter of the growth circle of *bacillus subtilis. subtillis.*

What is claimed is:

1. A reference blood filter paper for measuring the concentration of methionine in blood, comprising:
    filter paper infiltrated with blood containing a known concentration of methionine and at least one water-soluble, sulfur-containing antioxidant in an effective concentration to preserve said methionine, said antioxidant being represented by general formula:

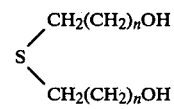

were n=1 or 2.

2. A reference blood filter paper as claimed in claim 1, wherein the concentration of said water-soluble, sulfur-containing antioxidant is in the range of 30 mM to 120 mM.

3. A reference blood filter paper as claimed in claim 2, wherein the concentration of said antioxidant is 35 mM to 60 mM.

* * * * *

UNITED STATES PATENT AND TRADEMARK OFFICE
CERTIFICATE OF CORRECTION

PATENT NO. : 4,367,286
DATED : January 4, 1983
INVENTOR(S) : Saito et al.

It is certified that error appears in the above-identified patent and that said Letters Patent is hereby corrected as shown below:

Column 5, line 59: Title in Table 3: "eruation" should read --ervation--

Column 8, line 25: "subtilis" is repeated. The second occurence of "subtillis" should be deleted.

Signed and Sealed this

Twentieth Day of December 1983

[SEAL]

Attest:

GERALD J. MOSSINGHOFF

Attesting Officer          Commissioner of Patents and Trademarks